(12) United States Patent
Joo et al.

(10) Patent No.: US 9,610,132 B2
(45) Date of Patent: Apr. 4, 2017

(54) SURGICAL INSTRUMENT FOR ASSISTING IN DISTINGUISHING ANTERIOR CAPSULE DURING CATARACT SURGERY

(71) Applicant: The Catholic University of Korea Industry-Academic Cooperation Foundation, Seoul (KR)

(72) Inventors: Choun-Ki Joo, Seoul (KR); Dong Jin Chang, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/907,569

(22) PCT Filed: Jul. 25, 2014

(86) PCT No.: PCT/KR2014/006800
§ 371 (c)(1),
(2) Date: Jan. 26, 2016

(87) PCT Pub. No.: WO2015/012634
PCT Pub. Date: Jan. 29, 2015

(65) Prior Publication Data
US 2016/0157952 A1    Jun. 9, 2016

(30) Foreign Application Priority Data

Jul. 26, 2013    (KR) .................. 10-2013-0089010

(51) Int. Cl.
*A61B 18/18*    (2006.01)
*A61B 90/30*    (2016.01)
*A61F 9/007*    (2006.01)

(52) U.S. Cl.
CPC .......... *A61B 90/30* (2016.02); *A61F 9/00736* (2013.01); *A61B 2090/309* (2016.02)

(58) Field of Classification Search
CPC .. A61B 18/18; A61B 2090/309; A61B 5/6821
USPC ....... 606/45, 47, 48, 49, 32, 37, 39, 41, 113, 606/166, 167
See application file for complete search history.

(56) References Cited

U.S. PATENT DOCUMENTS 8,157,797 B2 *   4/2012   Boukhny ............ A61F 9/00754
                                                                       606/45
9,173,771 B2 *  11/2015   Keller .................... A61B 17/32

* cited by examiner

*Primary Examiner* — Hung Dang

(57) ABSTRACT

The present invention relates to a surgical instrument for cataract surgery, and provides the surgical instrument for assisting in distinguishing the anterior capsule during cataract surgery, including a ring-shaped body; and a light source provided on a bottom surface portion of the body.

20 Claims, 4 Drawing Sheets

SURGICAL INSTRUMENT FOR ASSISTING IN DISTINGUISHING ANTERIOR CAPSULE DURING CATARACT SURGERY

RELATED APPLICATIONS

This application is a National Phase of PCT Patent Application No. PCT/KR2014/006800 having International filing date of Jul. 25, 2014, which claims the benfit of priority of Korean Patent Application No. 10-2013-0089010 filed on Jul. 26, 2013. The contents of the above applications are all incorporated by reference as if fully set forth herein in their entirety.

FIELD AND BACKGROUND OF THE INVENTION

The present invention relates to a surgical instrument for assisting in distinguishing an anterior capsule during a cataract surgery, and more specifically, to a surgical instrument including a light source such as an LED, and to irradiate with light from a side of the cornea by coming in contact with the cornea of an eye during the cataract surgery.

BACKGROUND ART

In an eye, an eye lens which is a transparent organ exists behind an iris and serves as a principal refraction organ. Light entering the eye refracts while passing through the eye lens, and forms an image on a retina, and when this eye lens becomes cloudy so as to hinder light from passing, the resulting foggy vision is known as a cataract disease. Depending on the cloudy part, a cataract disease is classified as a posterior polar cataract, a posterior subcapsular cataract, a cortical cataract, a lamellar cataract, and a nuclear cataract.

When normal activity becomes difficult due to a cataract disease, a surgery is necessary. A surgery involves procedures for removal of cloudy material within an eye lens and a subsequent insertion of an artificial lens suitable for each individual's eyesight.

During a cataract surgery, an anterior capsule (a membrane enveloping the eye lens) incision is important which determines success or failure of the surgery. Generally, in incising the anterior capsule during a cataract surgery, incision surfaces are made visible by illumination of a retro-reflection of light from a light source of a surgical microscope. However, for a serious cloudiness in an eye lens, observation of incision surfaces can be difficult. Thus, a method is necessary to overcome this problem.

SUMMARY OF THE INVENTION

The present invention is directed to providing a surgical instrument to facilitate microscopic observation of incision surfaces of an anterior capsule exposed during incising by increasing contrast of the incision surfaces by irradiating with light from a side of the cornea.

To solve the problem, according to an aspect of the present invention, a surgical instrument for assisting in distinguishing of anterior capsule during a cataract surgery includes a ring-shaped body, and a light source at a bottom surface portion of the body.

Also, the light source may be a light-emitting diode (LED).

Also, a plurality of light sources may be provided in a circumferential direction of the body.

Also, at least one light source may be provided to irradiate with light through a bottom a surface of the body.

Also, at least one light source may be provided to irradiate with light through a side surface of the body.

Also, the plurality of light sources may be arranged asymmetrically.

Also, the body may have an open space formed by cutting off the ring shape.

Also, a plurality of open spaces may be provided in the circumferential direction of the body.

Also, a width of the open space of the body may be provided to increase towards the bottom surface portion.

Also, the width of the open space of the body may be provided to decrease towards the bottom surface portion.

Also, the width of the open space of the body may be provided to remain constant towards the bottom surface portion.

Also, the body may include a bottom surface portion, a lower compartment having a ring shape, and an upper compartment having a ring shape provided above a second compartment.

Also, an open space formed in a gap of the ring shape may be provided on the lower compartment.

Also, the plurality of open spaces may be provided in a circumferential direction of the body.

Also, the upper compartment may be provided to form a closed curve in a circumferential direction of the body.

Also, the surgical instrument may further include a handle connected to the body.

Also, the light source may be powered by a built-in battery or an external power source.

Also, the bottom surface portion of the body contacts border areas of a cornea, and the light source is provided to irradiate with light from a side of the cornea.

Also, a slip preventing layer may be provided on the bottom surface portion of the body.

Also, a light source may be embedded inside of the bottom surface portion of the body.

Also, a plurality of vacuum holes may be provided on the bottom surface portion of the body.

Also, the vacuum holes may be connected to a vacuum pump provided on the body or a vacuum pump separately provided from the body.

A surgical instrument according to the present invention allows efficient observation of an anterior capsule during cataract surgery to assist in incising of the anterior capsule and thus ultimately, vision improvement after the cataract surgery can be maximized, and post-surgery complications can be minimized.

DESCRIPTION OF SPECIFIC EMBODIMENTS OF THE INVENTION

Hereinafter, the present invention will be described in detail with reference to the accompanying drawings.

Figure 1:
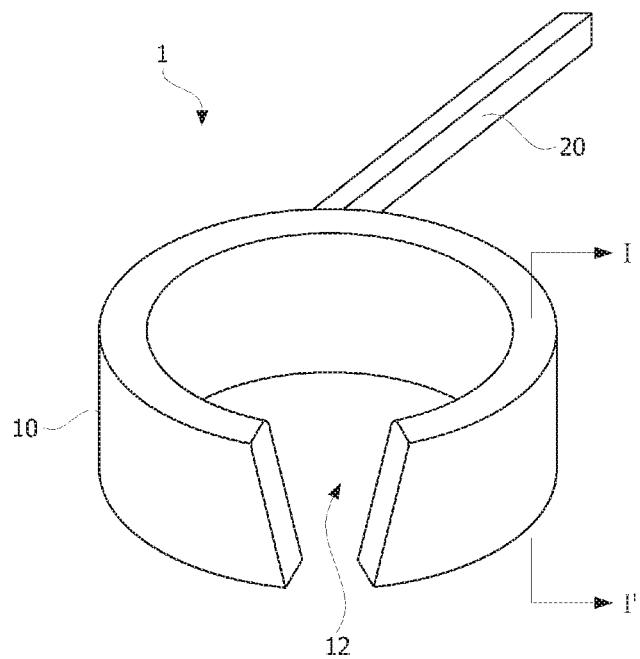
FIG. 1 is a perspective view of a surgical instrument for assisting in distinguishing an anterior capsule during a cataract surgery according to the present invention.

FIG. 1 is a perspective view of a surgical instrument 1 for assisting in distinguishing an anterior capsule during a cataract surgery according to the present invention.

According to FIG. 1, the surgical instrument 1 according to an embodiment of the present invention includes a body 10 and a light source 30.

Also, the surgical instrument 1 according to the present invention may include the body 10, a handle 20, and the light source 30, and the surgical instrument 1 may approximately be shaped like a dipper with an opening at the bottom.

The body 10 has a ring shape, that is, a structure with both upper and lower portions open so that the surgical instrument 1 can approach a cornea 40. To be able to accommodate surrounding the cornea 40, the body 10 has a diameter close to or larger than a diameter at the lower portion of the cornea 40 so as to envelop and accommodate the cornea 40.

The body 10 may be made of a metal, a plastic, etc. A type of the meal is not particularly limited, but a biocompatible metal is preferred. As an example of a biocompatible metal, precious metal alloys of Au and Ag, etc., Co alloys, Ni—Cr-based stainless steel, pure titanium, Ti alloys, etc., may be used. A type of plastic is not particularly limited, but a biocompatible plastic is preferred. As an example of a biocompatible plastic, Avcothane in which polyurethane and polydimethylsiloxane are copolymerized, a copolymer of styrene and polyamine, etc. may be used.

The body 10 may have an open space 12 formed in a gap of the ring shape. By giving flexibility to the body 10, the open space 12 allows expansion of the body 10, and thus allows adjusting a size of the body 10 depending on a size of the cornea 40. That is, the open space 12 serves to facilitate insertion of the body 10 of the surgical instrument 1 into the cornea 40. In addition, the open space 12 also provides a space for other surgical instruments, for example, a cutting instrument, to be introduced.

According to FIG. 1, the width of the open space 12 may be provided to decrease towards the bottom surface of the body. According to an embodiment of the present invention, both free ends of a gap of the body 10 may slope downward.

The surgical instrument 1 may have the handle 20 coupled to the body 10. The handle 20 facilitates carrying and utilizing the surgical instrument 1, and particularly allows a surgical procedure to be performed in a comfortable posture. The handle 20 and the body 10 may be integrally formed, and also may be combined by means of assembly, welding, adhesion, etc. The handle 20 may be made of a material the same as, or differing from, that of the body 10. Also, the plurality of handles 20 may be provided in a circumferential direction of the body 10. In such a case, a plurality of handles 20 may have different lengths from each other. Further, the plurality of handles 20 may be coupled to the body 10 at different angles from each other.

Figure 2:
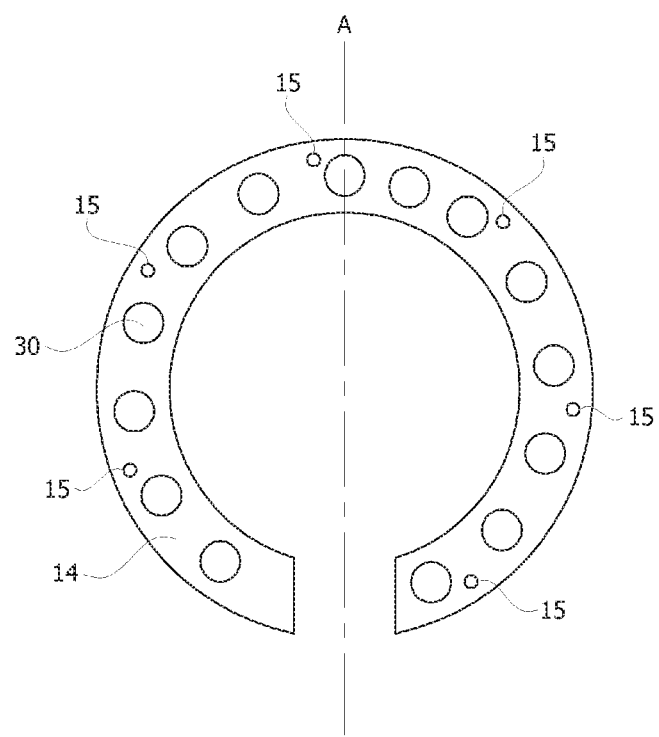
FIG. 2 is a bottom view of a body of the surgical instrument according to the present invention.

FIG. 2 is a bottom view of the body 10 of the surgical instrument 1 according to the present invention, and a plurality of light sources 30 may be provided on a bottom surface portion 14 of the body 10. The light source 30 may be provided to be embedded in the bottom surface portion 14. Alternatively, the light source 30 may be provided to protrude from the bottom surface portion 14. In this document, the bottom surface portion 14 includes a bottom surface of the body 10. In addition, the bottom surface portion 14 may include at least a portion of a side surface adjacent to the bottom surface of the body 10.

The bottom surface portion 14 of the body 10 comes in contact with border regions (edges) of the cornea 40. By providing the light source 30 on the bottom surface portion 14 of the body 10, the light source 30 may irradiate the cornea 40 with light from a side surface of the cornea 40. Also, the bottom surface portion 14 of the body 10 may have a slip preventing layer.

The light source 30 is not particularly limited, but a light-emitting diode (LED) light source may preferably be used. Since the LED light source, compared to other light sources including tungsten light bulbs, neon light source, etc., is highly efficient in converting electricity to light, does not generate heat, and is small and light, the LED light source has a long life. In addition, there is a negligible delay between turn on and light emission, its response time is good, and it is able to be provided in a variety of shapes.

As shown in FIG. 2, the plurality of light sources 30 may be arranged in a lateral or vertical asymmetry with respect to an imaginary line A. By asymmetrically arranging the light sources 30, a contrast of incision surfaces of an anterior capsule when irradiating with light may be enhanced.

Alternatively, when incising an anterior capsule of an eye lens, to distinguish contrast of incision surfaces of the anterior capsule, a wavelength of light may be adjusted. For example, by using a light source with a specifically necessary wavelength and adjusting the wavelength, contrast distinction of the anterior capsule incision surfaces may be effectively enhanced.

The light source 30 of the surgical instrument 1 may be powered by a built-in battery (not shown) and/or external power (not shown) of the surgical instrument 1, and a wire may be installed inside and/or outside of the surgical instrument 1 to connect to a power source.

Figure 3:
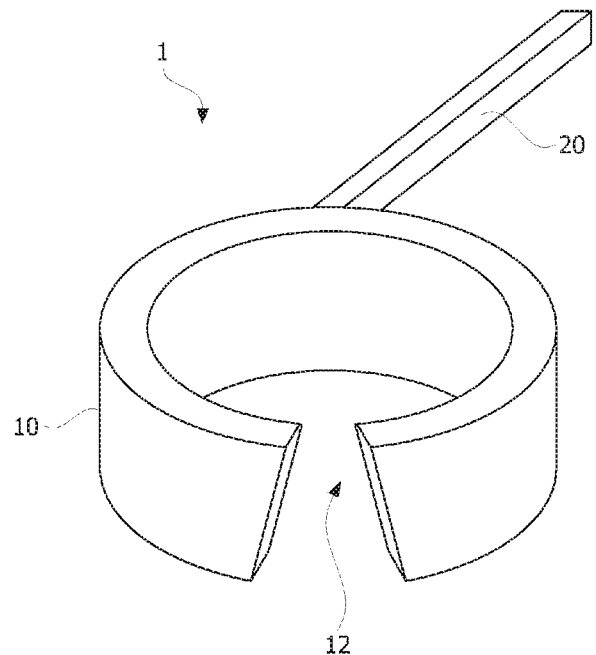
FIGS. 3, 4 and 5 are perspective views of a surgical instrument for assisting in distinguishing an anterior capsule during a cataract surgery according to various embodiments of the present invention.
Figure 4:
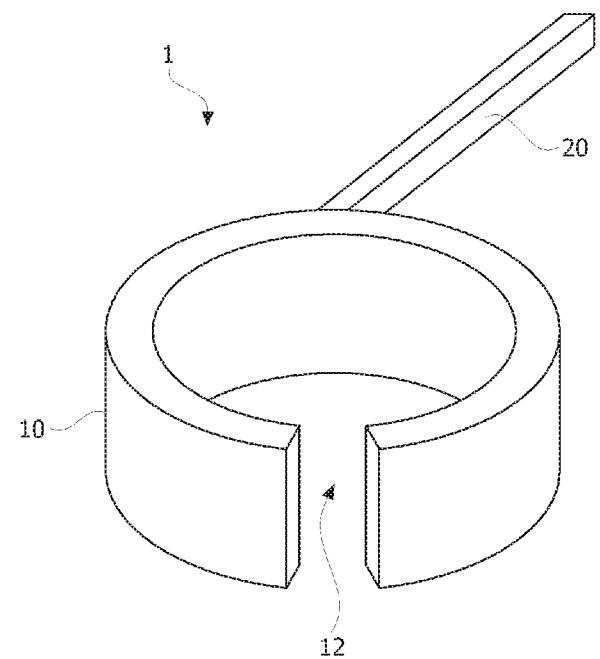
Figure 5:
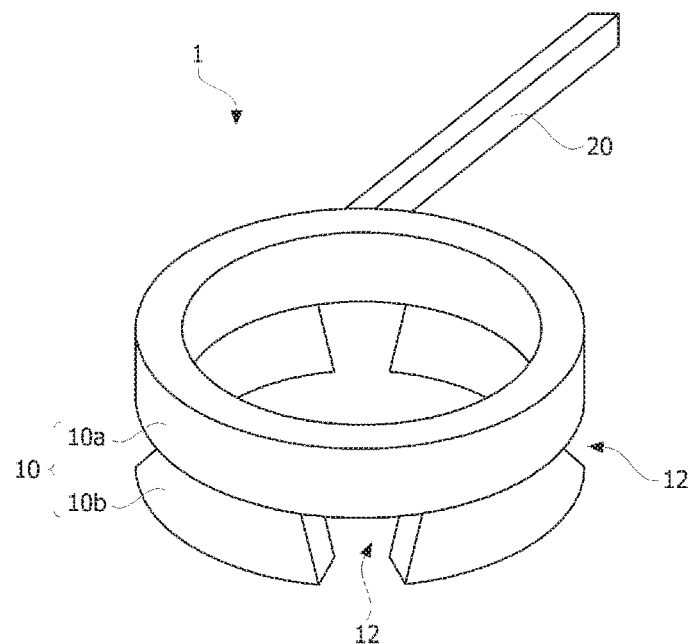

FIGS. 3, 4 and 5 illustrate perspective views of surgical instruments for assisting in distinguishing an anterior capsule during a cataract surgery according to various embodiments of the present invention.

As shown in FIG. 3, a width of an open space may be provided to increase towards a bottom surface portion 14 of a body. According to an embodiment of the present invention, both free ends of a gap of a body 10 may be provided to slope upward.

As shown in FIG. 4, the width of the open space may be provided to remain constant towards the bottom surface portion 14 of the body. According to the embodiment of the present invention, both free ends of a gap of the body 10 may be provided to be parallel to each other.

As shown in FIG. 5, a body 10 includes a bottom surface portion 14, a lower compartment 10b having a ring shape, and an upper compartment 10a having a ring shape provided above the lower compartment 10b. Here, at the lower compartment 10b, an open space 12 formed by cutting off the ring shape may be provided. Also, the plurality of open spaces 12 may be provided in the circumferential direction of the body 10. At this point, a width of the open space 12 may be provided to increase, decrease, or remain constant towards a bottom surface portion 14 of the body 10.

In addition, the upper compartment 10a may be provided to form a closed curve in the circumferential direction of the body 10. That is, in the upper compartment 10a, the open space 12 may not be provided. Additionally, the upper compartment 10a and the lower compartment 10b may be integrally formed. Additionally, the above described handle 20 may be provided on the upper compartment 10*a*.

Figure 6:
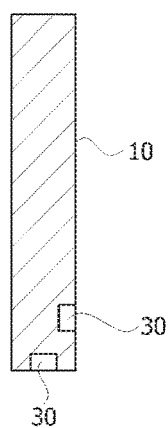
FIGS. 6 and 7 are cross-sectional views taken along line I-I' of FIG. 1.
Figure 7:
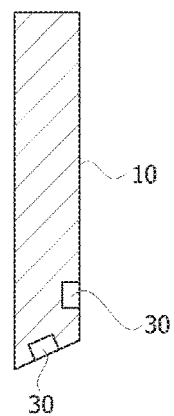

FIGS. 6 and 7 are cross-sectional views of FIG. 1 taken along line I-I'.

As described above, the plurality of light sources 30 may be provided on the bottom surface portion 14 of the body 10. The light source 30 may be provided to be embedded in the bottom surface portion 14.

As shown in FIGS. 6 and 7, at least one light source may be provided to irradiate with light from a bottom surface of the body 10. Also, at least one light source may be provided to irradiate with light from a side surface of the body.

As shown in FIG. 6, the bottom surface of the body 10 may be provided to be parallel to a top surface thereof. On the other hand, as shown in FIG. 7, the bottom surface of the body 10 may be provided to be sloped toward to the top surface thereof.

Figure 8:
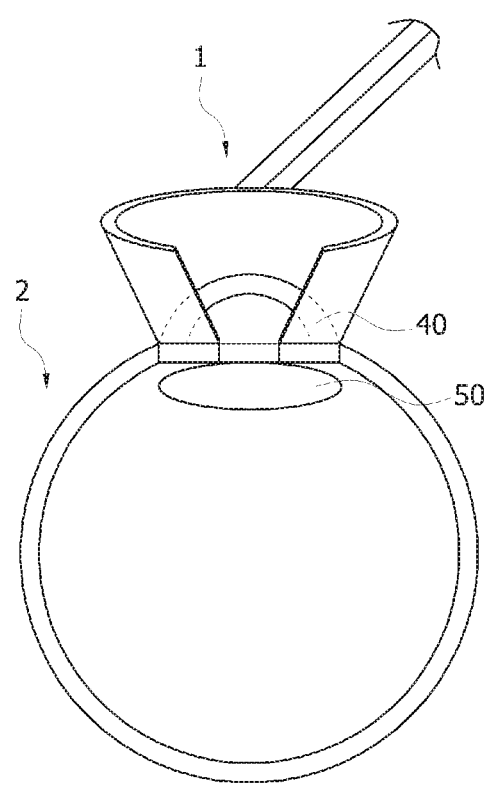
FIG. 8 illustrates a used state of the surgical instrument according to the present invention.

FIG. 8 illustrates a use of a surgical instrument 1 according to the present invention. An eye 2 includes a cornea 40 and an eye lens 50, etc. The cornea 40 is a front outermost organ in the eye 2 and is transparent without blood veins. The eye lens 50 is a transparent colorless organ which exists in the front of the eye 2 and is in a convex lens shape, and focuses light. An anterior capsule (not shown) of the eye lens 50 is a membrane that envelops the front of the eye lens 50.

When the surgical instrument 1 according to the present invention is disposed as shown in FIG. 8 so that the cornea 40 is inserted into an interior portion, the bottom surface portion 14 of the body 10 comes in contact with border regions (edges) of the cornea 40. Since the cornea 40 slightly protrudes and is approximately formed in a semicircle when viewed as a cross section, a light source 30 installed at the bottom surface portion 14 may irradiate an interior portion of the cornea 40 with light from side surfaces thereof. Then, using the surgical instrument 1 according to the present invention, surgical procedures including incising, etc., may be performed while observing the anterior capsule 50.

Alternatively, a plurality of vacuum holes 15 may be provided at the bottom surface portion 14 of the body 10. The plurality of vacuum holes 15 may be provided in the circumferential direction of the body 10. Also, each of the plurality of vacuum holes 15 may be provided at regular intervals in the circumferential direction of the body 10, so that suction force may be evenly applied.

In addition, the vacuum hole 15 may be connected to a vacuum pump that is provided at the body 10 or a vacuum pump separately provided from the body 10. Alternatively, when the vacuum pump is integrally provided with the body 10, the vacuum pump may receive electricity from a battery built into the body 10 or from an outside source.

Thus, when the bottom surface portion 14 of the body 10 comes in contact with the border regions (edges) of the cornea 40 and the vacuum pump is operated, the body 10 may be maintained in a contact state.

The surgical instrument 1 according to the present invention is a device for irradiating the interior of a cornea 40 with light from the edges of the cornea 40, allows effective observation of the anterior capsule of the eye lens 50 during a cataract surgery, assists in incising of the anterior capsule and thus ultimately, vision improvement after the cataract surgery can be maximized and post-surgery complications can be minimized.

The above described exemplary embodiments of the present invention are given as examples, and it shall be appreciated that various permutations and modifications of the described embodiments are possible by those skilled in the art to which the present invention pertains without departing from the scope of the invention.

Industrial Applicability

A surgical instrument according to the present invention allows efficient observation of an anterior capsule during cataract surgery to assist in incising of the anterior capsule and thus ultimately, vision improvement after the cataract surgery can be maximized, and post-surgery complications can be minimized.

What is claimed is:

1. A surgical instrument for assisting in distinguishing of an anterior capsule during a cataract surgery, comprising:
    a ring-shaped body; and
    a light source provided on a bottom surface portion of the body.

2. The surgical instrument of claim 1, wherein the light source is a light-emitting diode (LED).

3. The surgical instrument of claim 1, wherein a plurality of light sources are provided in a circumferential direction of the body.

4. The surgical instrument of claim 3, wherein at least one light source is provided to irradiate with light through a bottom surface of the body, and at least one light source is provided to irradiate with light through a side surface of the body.

5. The surgical instrument of claim 3, wherein the plurality of light sources are asymmetrically arranged.

6. The surgical instrument of claim 1, wherein the body has an open space formed by being cut off in a gap of the ring shape.

7. The surgical instrument of claim 6, wherein the plurality of open spaces are provided in a circumferential direction of the body.

8. The surgical instrument of claim 6, wherein a width of the open space increases towards the bottom surface portion of the body.

9. The surgical instrument of claim 6, wherein the width of the open space decreases towards the bottom surface portion of the body.

10. The surgical instrument of claim 6, wherein the width of the open space remains constant towards the bottom surface portion of the body.

11. The surgical instrument of claim 1, wherein the body includes a bottom surface portion, a lower compartment having a ring shape, and an upper compartment having a ring shape provided above a second compartment, and the lower compartment has an open space formed by cutting off the ring shape.

12. The surgical instrument of claim 11, wherein the plurality of open spaces are provided in the circumferential direction of the body.

13. The surgical instrument of claim 11, wherein the upper compartment forms a closed curve in the circumferential direction of the body.

14. The surgical instrument of claim 1, further comprising a handle connected to the body.

15. The surgical instrument of claim 1, wherein the light source is powered by a built-in battery or an external power source.

16. The surgical instrument of claim 1, wherein the bottom surface portion of the body comes in contact with border regions of a cornea, and the light source is provided to illuminate with light from a side of the cornea.

17. The surgical instrument of claim 1, wherein a slip preventing layer is provided on the bottom surface portion of the body.

18. The surgical instrument of claim 1, wherein the light source is embedded inside of the bottom surface portion of the body.

19. The surgical instrument of claim 1, wherein a plurality of vacuum holes is provided on the bottom surface portion of the body.

20. The surgical instrument of claim 19, wherein the vacuum holes are connected to a vacuum pump provided in the body or a vacuum pump separately provided from the body.

\* \* \* \* \*